United States Patent [19]

Dal Moro et al.

[11] 4,325,941
[45] Apr. 20, 1982

[54] SOLID FORMULATIONS CONTAINING PHEROMONES AND METHOD OF USING SAME

[75] Inventors: Anacleto Dal Moro; Franco Pinamonti; Amedeo Capizzi, all of Milan, Italy

[73] Assignee: Montedison S.p.A., Milan, Italy

[21] Appl. No.: 267,395

[22] Filed: May 26, 1981

Related U.S. Application Data

[63] Continuation-in-part of Ser. No. 210,728, Nov. 26, 1980, abandoned.

[30] Foreign Application Priority Data

Nov. 29, 1979 [IT] Italy ............................... 27702 A/79

[51] Int. Cl.³ ............................................ A01N 17/14
[52] U.S. Cl. ...................................................... 424/84
[58] Field of Search .......................................... 424/84

[56] References Cited

U.S. PATENT DOCUMENTS

| | | | |
|---|---|---|---|
| 2,123,929 | 7/1938 | Bousquet | 424/174 |
| 2,800,457 | 7/1957 | Green et al. | 252/316 |
| 2,800,458 | 7/1957 | Green | 252/316 |
| 3,097,128 | 7/1963 | Sprinkle et al. | 424/84 |
| 3,577,515 | 5/1971 | Vandegaer | 424/32 |
| 3,791,983 | 2/1974 | Maierson | 424/84 |
| 3,954,968 | 5/1976 | McKibben | 424/84 |
| 3,961,051 | 6/1976 | Emodi | 424/174 |
| 3,962,428 | 6/1976 | Emodi | 424/174 |
| 4,017,030 | 4/1977 | Coplan et al. | 239/44 |
| 4,160,335 | 7/1979 | Von Kohorn et al. | 424/84 |
| 4,171,355 | 10/1979 | Stubbs et al. | 424/174 |
| 4,219,542 | 8/1980 | Klun et al. | 424/84 |

OTHER PUBLICATIONS

"Controlled Release of Pheromones Through Multi-Layered Polymeric Dispensers Agis F. Kydonieus and Inja K. Smith–Hercon Div., Health–Chem. Corp., New York and Morton Beroza, M. Beroza & Assoc., Silver Spring, Maryland, pp. 283–294 inc.

*Primary Examiner*—Donald B. Moyer

[57] ABSTRACT

There are disclosed solid formulations containing, as an active substance, a sex pheromone; as main vehicles, a carrier having absorbing properties and another carrier having adsorbing properties, and, furthermore, a wetting agent, a dispersant, a sticker, an ultraviolet (U.V.) stabilizer, an antioxidant and, optionally, a film-forming resin. Such formulations are utilized to control insects.

In particular, the disclosed formulations contain, as an active substance, a sex pheromone of insects and, as a main vehicle, a mixture composed of a carrier having absorbing properties, and of another carrier having adsorbing properties, and are utilized to prevent insects from mating (mating disruption).

21 Claims, No Drawings

SOLID FORMULATIONS CONTAINING PHEROMONES AND METHOD OF USING SAME

This application is a continuation-in-part of Ser. No. 210,728, filed on Nov. 26, 1980, now abandoned.

BACKGROUND OF THE INVENTION

In recent years, pheromones have become very important in the research of methods useful to control the insects causing infestations of agrarian cultivations. As compared with conventional agents, they offer the advantage of an outstanding selectivity for one species only or for a restricted number of closely related species, without affecting other non-infesting species. It is, therefore, at least theoretically possible to fight a certain pest with the aid of pheromones with minimal disturbance of the ecological equilibrium.

Pheromones are secreted outside the insect body and, depending on the type of reaction they cause, can be divided into aggregation, tracing, sexual, alarming, etc., pheromones.

The most diffused and interesting pheromones, due to the possibilities of application in the control of insects, are the sex pheromones which are most frequently secreted by females, but also by males, and attract the individuals of the opposite sex for copulation. The use of pheromones for controlling the insects is based on the principle that little amounts of such compounds, obtained by synthesis, cause the same reactions as are induced by the male or female insects secreting the natural attractant.

In practice, the synthesized sex pheromones are used both to survey the development of the harmful species population and to control the harmful species by mating disruption. The former type of application (monitoring) permits to follow, by means of periodic samplings with small cage-traps, the density variations of the harmful insect population in order to forecast the time in which the "harmfulness threshold" will be reached. In the latter type of application, the sex pheromones are used to partially or fully substitute insecticides and to directly control the insects by modifying their behavior (mating disruption).

The techniques utilized to this last-mentioned purpose are two: mass trapping and confusion. The former technique (mass trapping) is directed to attracting and catching as many insects as possible by means of small cage-traps. The latter technique (confusion technique) consists in spreading the pheromone in the atmosphere in such way as to render the males or females incapable of "feeling" and locating the individuals of the opposite sex, so hindering copulation.

In practice, the attractant can be diffused by distributing the product in various properly spaced points of the concerned area, or by uniformly spraying it on the whole cultivation. In the first case use is made of evaporators containing the pheromone, which is included or incorporated in materials of various nature suited to cause volatilization to occur at a proper and constant rate. Such methods, however, are rather expensive because of the high cost of both evaporators and labor.

A less expensive and complicated method is that of distributing the pheromone all over the area by atomizing it from the ground or in the air and using special controlled-release formulations.

Some known systems of slow-release formulations are aqueous suspensions of pheromone-containing microcapsules having walls made of polyamides (U.S. Pat. No. 3,577,515) or of gelatin (U.S. Pat. Nos. 2,800,457; 2,800,458), or they may be multilayer polymeric systems incorporating the pheromone, (A.C.S. 33, 1976, pg. 283) or hollow fiber systems consisting of a capillary from an open end of which the pheromone is released and caused to volatilize (U.S. Pat. No. 4,017,030).

Such systems are particularly complicated as regards both the preparation and, chiefly, the subsequent distribution in the field.

A further drawback of those known systems is that of providing a non-constant pheromone release kinetics, just due to the model of the capsule.

The rate at which the pheromone is released is affected not only by the amount of the active compound and the chemical composition of the capsules and of the other formulation components, but also by environmental factors, such as temperature, light, humidity.

A desirable characteristic of a formulation emitting the pheromone in an amount sufficient to permeate the atmosphere and to obtain the effect of hindering copulations is a controlled, complete and constant release over a proper stretch of time.

THE PRESENT INVENTION

It is an object of the present invention to provide solid formulations with a controlled, complete and constant sex pheromone release, capable of preventing as much as possible insect copulations.

It has been observed that formulations containing the active substance carried on an inert absorbent provided a constant and complete but quick pheromone release, while formulations containing the active substance carried on an inert absorbent provided a slow but incomplete and non-constant pheromone release (see Example 2 infra, compositions 9, 10, 11, 12).

We have now found, surprisingly, that formulations containing the active substance carried on mixtures of absorbing and of adsorbing carriers in the presence of proper stabilizing agents give rise to a controlled, complete and, with an optimum approximation, constant pheromone release.

According to the invention there are provided solid formulations containing, as an active substance, a sex pheromone of insects, as a main vehicle, a carrier consisting of an inert material having absorbing properties and of an inert material having adsorbing properties, and, furthermore, a wetting agent, a dispersant and a sticker, an U.V. stabilizer and an antioxidant, having the following composition, to 100%:

| | |
|---|---|
| A - Active substance (sex pheromone) | 0.5–10% by weight |
| B - Inert material with absorbing properties | 20–50% by weight |
| C - Inert material with adsorbing properties | 10–50% by weight |
| D - Dispersant, wetting agent, sticker | 5–15% by weight |
| E - U.V. stabilizer | 0.5–10% by weight |
| F - Antioxidant | 0.5–10% by weight |

It is also possible to coat the particles of the carrier containing, in the adsorbed form, the active substance, the antioxidant and the stabilizer, with film-forming materials which further slow down the release of the active substance.

The formulations described herein provide a controlled, complete and constant release of the active substance. Said formulations are applied as wettable powders according to conventional modalities.

The main vehicles forming the inert materials which carry the active substance are, for example, as absorbing carriers, calcined fossil metal, kaolin, micronized attapulgites, talc, and as adsorbing carrier, activated carbon. The fossil meal has a composition based on silicates of Al, Fe, Ca, Mg, Na, K: typical examples are "Celite SSC" and "Celite 209". The kaolin has a composition mainly based on aluminum silicate, a typical example being "Argirek B22." A useful attapulgite has a composition based on silicates of Al, Mg, Ca, Fe, Na, K, a typical example being "Diluex".

The activated carbon used in the formulations of the invention is a microporous carbon obtained from natural products through a chemical or thermal activation process. Such processes facilitate the formation of molecular pores, so increasing the inside surface which surface exerts attractive effects on certain surrounding molecules of gas or of liquids and the attraction forces cause the adsorption phenomenon. The activated carbon employed is mainly characterized by a specific surface in the range of from 300 to 900 $m^2/g$. Activated carbons having a higher specific surface are used in lower amounts as compared with activated carbons having a lower specific surface.

The presence of a proper U.V. stabilizer and of a proper antioxidant in the formulations of the present invention is absolutely necessary in order to safeguard the chemical integrity of the active substance, to insure the stability of the pheromone in the formulation and to preserve the pheromone as long as possible when the treatment is carried out in the open field.

The selected U.V. stabilizers belong to the class of the high molecular weight derivatives of benzophenone, in particular 2-hydroxy-4-octyloxy-benzophenone of the formula:

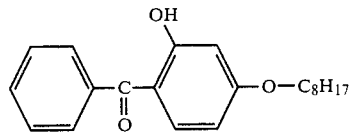

The selected antioxidants belong to the class of the derivatives of 2,6-di-terbutylphenol, in particular 2,6-di-terbutylphenol propionate of stearyl and 2,6-di-terbutylphenol propionate of pentaerythritol.

Some examples of suitable wetting agents, dispersants and stickers are the compounds based on mixtures of methacrylic polymer, nonylphenol polyoxyethylates and sodium lignosulphonate.

The film-forming resins generally used, and the use of which is optional, are composed of compounds based on terpene polymers, or of mixtures of chlorinated derivatives of natural rubber, in amounts of from 10 to 30% by weight.

The methodology followed for preparing the formulations of the present invention is in accordance with the known principles of the art.

The sex pheromones constituting the active substance of the formulations according to this invention may be pheromones of different insects such as, for example:

(E,E)-8,10-dodecadienol, pheromone of *Laspeyresia pomonella L.*, (Z)-8-dodecenyl acetate, pheromone of *Grapholitha molesta, Busk.*, (Z)-9-dodecenyl acetate, pheromone of *Clysia ambiguella Hb.*, (E,Z)-7,9-dodecadienyl acetate, pheromone of *Lobesia botrana Den & Schiff*, (Z)-11-tetradecenyl acetate and (E)-11-tetradecenyl acetate, pheromone of *Archips podanus Scop.*, (Z,E)-9,11-tetradecadienyl acetate, pheromone of *Spodoptera littoralis Boisd.*, (Z)-11-hexadecen-1-al, pheromone of *Heliothis armigera Hb.*, (E)-11-tetradecen-1-al, pheromone of *Choristoneura fumifera*, (Z)-11-hecadecen-1-al and (Z)-9-tetradecen-1-al, pheromone of *Heliothis virescens*, and others.

The controlled-release formulations offer, among other advantages, the possibility of being applied with the same methods and equipment as are commonly used for wettable powders, which results in a sensible economic advantage and in easy handling for all users.

The chemical compounds which are components of insect sex pheromones can be prepared according to known procedures. They have been described in various publications, examples of which are hereinbelow reported:

M. Beroza et al., Science 183, 89 (1974) [pheromone of *Laspeyresia Pomonella*]

W. L. Roelofs et al., Nature 224, 723 (1969) [pheromone of *Grapholiteha Molesta*]

B. F. Nesbitt et al., Nature Nev. Biol. 244, 208 (1973) [pheromone of *Spodoptera Littoralis*]

J. C. Person et al., J. Insect Physiol. 20, 1181 (1974) [pheromone of *Archips Podanus*]

H. Arn et al., Z. Naturforsch. 31C, 499(1976) [pheromone of *Clysia Ambiguella*]

H. Arn et al., Z. Naturforsch. 30, 722(1975) [pheromone of *Lobesia Botrana*]

C. J. Sanders et al., Can. Entomol 108, 1285 (1976) [pheromone of *Choristoneura Fumiferana*]

Ohta Kyuji et al., Agric. Biol. Chem. 40(9), 1897(1976) [pheromone of *Heliothis Armigera*]

H. M. Flint et al., J. Econ. Entomol. 72,798 (1979) [pheromone of *Heliothis Virescens*].

As herein before reported the inert materials with absorbing properties are, for example, calcined fossil meal, kaolin and micronized attapulgite. The commercially available products can suitably be used in the formulations object of the invention.

Characteristics of the fossil meal are: bulk density comprised between 120 and 150 g/l, specific surface comprised between 4–6 $m^2/g$, pH of 10% aqueous suspension comprised between 6 and 8.

"Celite SSC" and "Celite 209" used in the examples are fossil meals with characteristics according to those above reported. The absorbing material named kaolin has the following characteristics: bulk density 320–460 g/l, specific surface 3–5 $m^2/g$, pH of 10% aqueous suspension 4–8.

"Argirek B 22" used in the examples is a kaolin with characteristics according to those hereabove reported.

Attapulgite is an inert material having the following characteristics: bulk density 150–300 g/l, specific surface 150–300 $m^2/g$. "Diluex" used in the examples is a micronized attapulgite whose characteristics are in accordance with those hereabove reported.

Other inert materials used in the examples are colloidal silica (bulk density 100–180 g/l, specific surface 150–200 $m^2/g$) such as "Vessalon S" and talc consisting essentially of a mixture of silicates (bulk density 450–800 g/l, specific surface 2–4 $m^2/g$).

The inert material with adsorbing properties used in the formulations object of the invention consists essentially of activated carbon (charcoal) having a specific surface comprised between 300 and 900 m²/g. The commercially available activated carbons having a specific surface in the above mentioned range can be suitably used.

A high degree of purity in the absorbing and adsorbing materials does not represent an essential feature for the scope of the invention and the commercially available products can be conveniently used.

The formulations object of the invention contain also antioxidant products chosen amongst the derivatives of 2,6-di-ter.butylphenol having antioxidant properties. Particularly usefull are 2,6-di-ter.butylphenol propionate of stearyl and of pentaerythritol [tetrakis-hydroxymethyl-metane $C(CH_2OH)_4$]. 2,6-di-ter.butylphenol propionate of stearyl is a name often used to indicate the ester of 3-(3,5-di-tert.-butyl-4-hydroxy-phenyl)-propionic acid with stearic alcohol and having the formula:

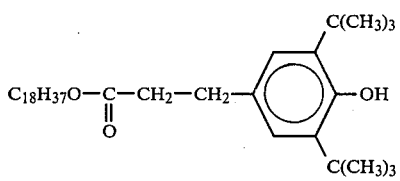

Similarly, 2,6-di-ter.butylphenol propionate of pentaerithritol indicates the tetrakis ester of 3-(3,5-di-tert.-butyl-4-hydroxy-phenyl)-propionic acid with pentaerithritol [$C(CH_2OH)_4$], having the formula

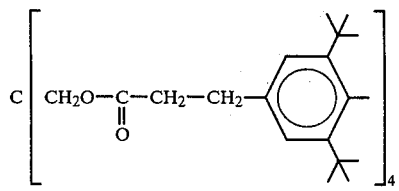

Further additives to be used in the formulations object of the invention are wetting agents, dispersants and stickers.

Suitable wetting agents are polyoxyethylated alkyl phenols and particularly polyoxyethylated nonylphenol containing 40-80 moles of ethylene oxide per mole of nonylphenol.

As a sticker, sodium polymethacrylate with molecular weight comprised between 10,000 and 40,000, can be used.

"Polymer PS 50" used in the examples is a commercially available mixture of polymethacrylate and polyoxyethylated nonyl phenol in the ratio 9:1.

Examples of dispersants which can be used in the formulations object of the invention are sodium lignosulphonates having a sulphonation degree comprised between 0.5 and 5. "Reax 45 A" used in the examples is a commercially available sodium lignosulphate whose characteristics are comprised in the hereabove reported range.

The wetting agent, sticker and dispersant can be used in the formulations object of the invention as a mixture consisting of 1–10% by weight of wetting agent, 50–94% by weight of sticker and 5–40% by weight of dispersant, the total being 100%.

An amount of such mixture comprised between 5 and 15% by weight is used in the formulations.

The use of said additives is related to the fact that the formulations object of the invention are in the form of wettable powder. The specific compounds hereabove mentioned as wetting agents, stickers and dispersants have been found to be particularly suited for the described formulations, without being a critical feature.

Terpene polymers consist essentially of polymerized pinene, having a softening comprised between 10° and 135° C. and a molecular weight comprised between 100–1300. "Picolite S 85" is an example of such polymers.

The chlorinated derivatives on natural rubber consist of chlorinated natural rubber having a content in chlorine of about 65–68% by weight and whose monomeric units are ($CH_5H_7Cl_3$) and ($C_5H_6Cl_4$), the viscosity of a 20% solution in toluene ranges between 5 and 180 cps (Hottler method).

"Chlortex 70" used in the examples is a chlorinated natural rubber whose characteristics are in the range hereabove reported.

The following examples are given to illustrate the present invention in more detail and are not intended to be limiting.

EXAMPLE 1

This example reports tests carried out to find the most suitable stabilizers.

100 g of the compositions 1 to 10 reported in Table I were prepared by depositing, from a solution in $CH_2Cl_2$, the active substance (henceforth called a.s.) and the possible stabilizers on various carriers, and by successively evaporating the solvent.

50 g of such compositions were kept for 14 days at room temperature and 50 g were kept in a thermostat at 40° C. At the end of such period the residual a.s., after extraction with n-hexane, was evaluated by gas-liquid chromatographic analysis.

TABLE I

| COMPONENTS | | 1 | 2 | 3 | 4 | 5 | 6 | 7 | 8 | 9 | 10 |
|---|---|---|---|---|---|---|---|---|---|---|---|
| Z, E9,11C$_{14}$Ac (a.s.) | (1) | 5 | 5 | 5 | 5 | 5 | 5 | 5 | 5 | 5 | 5 |
| Vessalon S | (2) | 95 | | | | | | | | | |
| Celite SSC | (3) | | 95 | | | | | 90 | 90 | 90 | 85 |
| Argirek B22 | (4) | | | 95 | | | | | | | |
| Talc 5/0 | | | | | 95 | | | | | | |
| Activated carbon in powder form | | | | | | | 95 | | | | |
| BHT | (5) | | | | | | | 5 | | | |
| Irganox 1010 | (6) | | | | | | | | 5 | | 5 | 5 |
| U.V. 531 | | | | | | | | | | 5 | 5 | 5 |
| Degradation in % after 14 days at: | | | | | | | | | | | |

TABLE I-continued

| COMPONENTS | | COMPOSITIONS | | | | | | | | | |
|---|---|---|---|---|---|---|---|---|---|---|---|
| | | 1 | 2 | 3 | 4 | 5 | 6 | 7 | 8 | 9 | 10 |
| | room temp. | 70% | 83% | 80% | 20% | 43% | 0 | 0 | 0 | 0 | 0 |
| | 40° C. | 70% | 82% | 82% | 29% | 50% | 4.4% | 3.8% | 2.4% | 0 | 0 |

Notes to Table I:
(1) Pheromone of *Spodoptera littoralis* (Z,E)-9,11-tetradecadienyl acetate
(2) "Vessalon S" - registered trademark of Degussa (Germany) - Colloidal silica
(3) "Celite SSC" - registered trademark of Johns-Manville - fossil meal
(4) "Argirek B22" - registered trademark of Argirek, Montguyon - kaolin
(5) BHT - 2,6-di-terbutyl-p-hydroxytoluene
(6) "Irganox 1010" - 2,6-di-terbutylphenol propionate of pentaerythritol
(7) U.V. 531 - 2-hydroxy-4-n.octyloxy benzophenone The best effect attained with the antioxidant/U.V. stabilizer of samples 9 and 10 was further confirmed by the successive test carried out under an U.V. lamp.

Samples 6, 7, 8, 9, 10 were placed under a solar spectrum lamp emitting ultraviolet radiations at distances equal to 20 cm at a temperature of 40° C. At different times a portion of the sample was drawn and the residual active substance was subjected to gas liquid chromatographic analysis after extraction with n-hexane. The results are recorded in Table II.

TABLE II

| Sample | a.s.: residue % after exposure time (minutes) | | | |
|---|---|---|---|---|
| No. | 0 | 360 | 930 | 2460 |
| 6 (1) | 100% | 47.4% | 0 | — |
| 7 | 100% | 83.5% | 20.5% | 1.5% |
| 8 | 100% | 91.6% | 15.5% | 0.2% |
| 9 | 100% | 87.0% | 60.0% | 14.3% |
| 10 | 100% | 88.1% | 50.9% | 16.1% |

Note to Table II:
(1) After 360 minutes BHT was reduced to 9.3% of the initial amount which means that BHT, though it stabilizes the a.s. in the formulation, does not retain the stabilizing effect during the exposure, owing to its rapid sublimation.

EXAMPLE 2

Release tests of (Z,E)-9,11 $C_{14}Ac$ stabilized with "Celite SSC" with activated carbon in powder form and with mixtures of same 100 g of each of the compositions 9a, 10a (compositions according to example 1), 11 and 12 recorded in Table III were prepared by depositing, from a solution in $CH_2Cl_2$, the active substance and the stabilizers on different carriers and by successively allowing the solvent to evaporate. The samples of Table III were then subjected in a cell to the following conditions:
temperature = 30° C.;
artificial lighting: 15 hours to 24 hours;
air change = 160 m³/h corresponding to 6 total changes/hour of the air in the cell.

At different times, samples were drawn and, after extraction with n-hexane, the percentage of residual a.s. was examined, with the results recorded in Table III.

TABLE III

| Components | Composition | | | |
|---|---|---|---|---|
| | 9a | 10a | 11 | 12 |
| (Z,E)-9,11 $C_{14}Ac$ | 5 | 5 | 5 | 5 |
| Irganox 1010 | 5 | 5 | 5 | 5 |
| U.V. 531 | 5 | 5 | 5 | 5 |
| Celite SSC | 85 | — | 10 | 60 |
| Activated carbon in powder (specific surface 300 m²/g) | — | 85 | 75 | 25 |

| | Data relevant to release tests: | | | | | | |
|---|---|---|---|---|---|---|---|
| Sample | a.s.: residue % after exposure time (hours) | | | | | | |
| No. | 0 | 30 | 118 | 169 | 185 | 300 | 430 | 500 |
| 9a | 100 | 93.7 | 75.8 | — | 61.0 | 41.2 | 16.8 | 0.0 |
| 10a | 100 | 95.5 | 86.7 | 83.3 | — | 83.3 | — | 84.4 |
| 11 | 100 | 95.2 | 83.7 | 76.2 | — | 53.8 | 34.4 | — |
| 12 | 100 | 93.6 | 84.1 | 80.5 | — | 64.7 | 54.1 | — |

EXAMPLE 3

Preparation of complete formulations:

100 g of formulations 13, 14, 15 indicated in Table IV were prepared by depositing, from a solution in $CH_2Cl_2$, the a.s. and the stabilizers on a prehomogenized mixture of activated carbon and Celite SSC. Successively the solvent was evaporated at room temperature. The indicated amounts of wetting agents, dispersants and stickers were then added. The mixture was homogenized in a mechanical mill. 50 g of such formulations were kept for 14 days at room temperature and 50 g were kept at 40° C. in a thermostat. At the end of such period the residual a.s., after extraction with n-hexane, was evaluated by gas liquid chromatographic analysis.

TABLE IV

| Components | Formulations | | |
|---|---|---|---|
| | 13 | 14 | 15 |
| (Z,E)-9,11-$C_{14}Ac$ (a.s.) | 5 | 5 | — |
| (Z)-11-$C_{14}$:Ac (a.s.) | — | — | 5 |
| IRGANOX 1010 | 5 | 5 | 5 |
| U.V. 531 | 5 | 5 | 5 |
| Polymer PS 50(RP10) (1) | 10 | 10 | 10 |
| REAX 45A (2) | 5 | 5 | 5 |
| Activated carbon (300 m²/g) | 25 | 40 | 35 |
| CELITE SSC | 45 | 30 | 35 |
| Degradation in % after 14 days at: | | | |
| R.T. | <0.1 | <0.1 | <0.1 |
| 40° C. | <0.1 | <1.0 | <1.0 |

Notes to Table IV:
(1) "Polymer PS 50 (RP10)" - Registered trademark of M/s ROL - mixture of methacrylic polymer and nonylphenol polyoxyethylate.
(2) "Reax 45A" = Registered trademark of M/s Westvaco - Na lignosulphonate.

EXAMPLE 4

Release tests carried out with complete formulations.

Release tests under the same conditions and following the same modalities as illustrated in Example 2 were carried out using formulations 13, 14, 15. The results obtained are reported in the following Table.

| Sample | Data relating to release tests a.s.: residue % after exposure time (hours) | | | | | | | | | | | | | | |
|---|---|---|---|---|---|---|---|---|---|---|---|---|---|---|---|
| No. | 0 | 95 | 120 | 168 | 264 | 432 | 550 | 600 | 624 | 940 | 1020 | 1104 | 1224 | 1368 | 1632 |
| 13 | 100 | 92.7 | — | 89.9 | 86.7 | 77.5 | — | — | 60.8 | — | — | 39.6 | 36.8 | — | — |
| 14 | 100 | | | | | | 78.0 | | | 61.7 | | | | 41.7 | 35.1 |
| 15 | 100 | | 89.6 | | | 74.2 | | 54.5 | | | | | | | |

EXAMPLE 5

Disorientation tests (confusion method) in Egypt.

Using formulation No. 13 of Example 4, disorientation tests were carried out on Spodoptera littoralis in Egypt, in the Faiyum district, locality Tamiya, in the periods from 8th to 30th June and from 1st to 6th July, 1979.

The formulation was applied on an area of 2 Feddan (1 Feddan=4,200 m²) sowed with cotton, in doses of 4 g of a.s./Feddan. Application was from the ground by means of a common sprayer, using a 0.2% suspension of the formulation in water.

The efficacy of the confusion method was determined by comparing the number of adult males caught in 4 traps baited with the same pheromone and placed respectively: two in the treated area and two in the adjoining untreated area (check).

The data are recorded in Table V.

TABLE V

| | | June 8, 1979 | 9 | 10 | 11 | 12 | 13 | 14[1] | 15 | 16 | 17 | 18 | 19 | 20 | 21 |
|---|---|---|---|---|---|---|---|---|---|---|---|---|---|---|---|
| TREATED | Trap 1 | 82 | 98 | 172 | 141 | 290 | 324 | 357 | 0 | 30 | 29 | 34 | 2 | 1 | 2 |
| AREA | Trap 2 | 32 | 29 | 62 | 74 | 97 | 132 | 197 | 0 | 21 | 6 | 46 | 1 | 4 | 0 |
| | Total catches | 114 | 127 | 134 | 215 | 387 | 456 | 554 | 0 | 51 | 35 | 80 | 3 | 5 | 2 |
| CHECK | Trap 3 | 59 | 33 | 112 | 89 | 162 | 195 | 448 | 67 | 213 | 195 | 325 | 25 | 4 | 13 |
| | Trap 4 | 51 | 77 | 216 | 229 | 256 | 147 | 395 | 36 | 397 | 281 | 257 | 246 | 131 | 186 |
| | Total catches | 110 | 100 | 328 | 318 | 418 | 342 | 843 | 103 | 610 | 476 | 582 | 271 | 135 | 199 |
| | T°C. max. | 35 | 33 | 35 | 37 | 40 | 42 | 40 | 39 | 39 | 40 | 41 | 43 | 43 | 43 |
| | min. | 21 | 23 | 21 | 22 | 22 | 22 | 23 | 23 | 23 | 22 | 23 | 24 | 25 | 24 |
| | Relative humidity % | 49 | 59 | 42 | 44 | 32 | 36 | 34 | 38 | 38 | 35 | 48 | 42 | 42 | 40 |
| | | 22 | 23 | 24 | 25 | 26 | 27 | 28 | 29 | 30 | July 1, 1979 | 2 | 3 | 4 | 5 | 6 |
| TREATED | Trap 1 | 1 | 0 | 0 | 1 | 1 | 0 | 0 | 0 | 0 | 0 | 0 | 0 | 0 | 0 | 0 |
| AREA | Trap 2 | 1 | 0 | 1 | 2 | 2 | 0 | 0 | 1 | 1 | 0 | 0 | 0 | 1 | 0 | 0 |
| | Total catches | 2 | 0 | 1 | 3 | 3 | 0 | 0 | 1 | 1 | 0 | 0 | 0 | 1 | 0 | 0 |
| CHECK | Trap 3 | 13 | 12 | 26 | 2 | 11 | 5 | 7 | 0 | 3 | 0 | 0 | 2 | 1 | 3 | 2 |
| | Trap 4 | 98 | 62 | 45 | 264 | 145 | 38 | 27 | 5 | 12 | 4 | 5 | 7 | 12 | 15 | 16 |
| | Total catches | 111 | 74 | 71 | 266 | 156 | 43 | 34 | 5 | 15 | 4 | 5 | 9 | 13 | 18 | 18 |
| | T°C. max. | 42 | 41 | 45 | 45 | 45 | 43 | 43 | 40 | 40 | 39 | 41 | 38 | 41 | 41 | 42 |
| | min. | 23 | 24 | 26 | 24 | 23 | 22 | 22 | 21 | 22 | 21 | 20 | 21 | 22 | 21 | 21 |
| | Relative humidity % | 46 | 42 | 42 | 52 | 52 | 49 | 48 | 50 | 42 | 42 | 50 | 50 | 44 | 44 | 46 |

[1]day of beginning of treatment carried out during the evening hours.

EXAMPLE 6

Use of absorbing inert materials of various types

Following the modalities of Example 3, compositions 16, 17 and 18 indicated in Table VI were prepared.

TABLE VI

| | Compositions | | |
|---|---|---|---|
| Components | 16 | 17 | 18 |
| (Z,E)-9,11 $C_{14}$Ac | 5 | 5 | 5 |
| Irganox 1010 | 5 | 5 | 5 |
| U.V. 531 | 5 | 5 | 5 |
| Reax 45A | 5 | 5 | 5 |

TABLE VI-continued

| | Compositions | | |
|---|---|---|---|
| Components | 16 | 17 | 18 |
| Polymer PS50 (RP10) | 10 | 10 | 10 |
| Carbon (300 m²/g) | 25 | 25 | 25 |
| Argirek B22 | 45 | — | — |
| Diluex in powder[1] | — | 45 | — |
| Celite SSC | — | — | 45 |

Note to Table VI.
[1]"Diluex" - Registered trademark of M/s Floridin - micronized attapulgites Such compositions were subjected to the release tests conforming to the modalities of Example 2.

Release tests: the same conditions as of Example 2.

| Sample | a.s.: residue % after exposure time (hours) | | | |
|---|---|---|---|---|
| No. | 0 | 384 | 600 | 912 |
| 16 | 100 | 82.0 | 78.5 | 55.6 |
| 17 | 100 | 82.6 | 71.9 | 53.7 |
| 18 | 100 | 81.3 | 70.5 | 51.35 |

EXAMPLE 7

According to the modalities of Example 3, the formulations indicated in Table VII were prepared.

TABLE VII

| | Compositions | | |
|---|---|---|---|
| Components | 19 | 20 | 21 |
| (Z,E) 9,11 $C_{14}$AC | 2.5 | 10 | 5 |
| U.V. 531 | 5 | 5 | 5 |

TABLE VII-continued

| Components | Compositions | | |
|---|---|---|---|
| | 19 | 20 | 21 |
| Irganox 1010 | 5 | 5 | 5 |
| Activated carbon 300 m²/g | 25 | 25 | |
| Celite SSC | 47.5 | 40 | 45 |
| Activated carbon 650 m²/g | | | 25 |
| Polymer PS50 (RP10) | 10 | 10 | 10 |
| Reax 45 A | 5 | 5 | 5 |

Release tests under the same conditions and according to the same modalities as in Example 2 were carried out with formulations 19, 20 and 21, with the results reported in the following tabulation.

| Sample No. | Data relating to release tests a.s.: residue % after exposure time (hours) | | | | | | | |
|---|---|---|---|---|---|---|---|---|
| | 0 | 120 | 200 | 340 | 500 | 800 | 1100 | 1480 |
| 19 | 100 | 94.51 | 87.76 | 89.02 | 83.5 | 77.2 | 69.19 | 59.49 |
| 20 | 100 | 97.6 | 96.05 | 92.31 | 90.82 | 87.19 | 79.61 | 69.47 |
| 21 | 100 | 96.57 | 94.96 | 91.76 | 92.9 | 89.2 | 85.35 | 76.88 |

EXAMPLE 8

According to the modalities of Example 3, the following compositions were prepared:

TABLE VIII

| | Composition | | | | | |
|---|---|---|---|---|---|---|
| | 22 | 23 | 24 | 25 | 26 | 27 |
| (E,E) 8,10 C$_{12}$-OH[1] | 2.5 | 5 | 5 | 10 | 5 | 5 |
| Activ. carbon 300 m²/g | 30 | 30 | 30 | 30 | | |
| Activ. carbon 650 m²/g | | | | | 45 | 30 |
| Celite SSC | 42.5 | 40 | 30 | 35 | 25 | 40 |
| Irganox 1010 | 5 | 5 | 5 | 5 | 5 | 5 |
| U.V. 531 | 5 | 5 | 5 | 5 | 5 | 5 |
| Picolite S85[2] | | | 10 | | | |
| Polymer PS50 (RP10) | 10 | 10 | 10 | 10 | 10 | 10 |
| Reax 45 A | 5 | 5 | 5 | 5 | 5 | 5 |

Notes to Table VIII:
[1] Pheromone of *Laspeyresia pomonella*;
[2] Registered trademark of M/s Chem-Plast, terpene polymers.

| Sample No. | Data relating to release tests: the same conditions of Example 2 a.s.: Residue % after exposure time (hours) | | | | | | |
|---|---|---|---|---|---|---|---|
| | 0 | 30 | 96 | 230 | 400 | 660 | 1260 |
| 22 | 100 | 94.2 | 93.3 | 88.8 | 81.7 | 75.9 | 53.6 |
| 23 | 100 | 95.8 | 96.2 | 88.5 | 83.4 | 74.2 | 45.9 |
| 24 | 100 | 98.6 | 95.2 | 91.1 | 83.8 | 79.3 | 57.3 |
| 25 | 100 | 96.4 | 96.2 | 91.3 | 86.0 | 82.1 | 64.6 |
| 26 | 100 | 99.5 | 98.3 | 92.6 | 90.4 | 91.1 | 80.0 |
| 27 | 100 | 98.8 | 98.8 | 92.0 | 88.8 | 82.9 | 72.7 |

EXAMPLE 9

According to the modalities of Example 3, the compositions indicated in Table IX were prepared.

TABLE IX

| | Composition | | | | |
|---|---|---|---|---|---|
| | 28 | 29 | 30 | 31 | 32 |
| (Z) 11-Hexadecenal[1] | 5 | 5 | 5 | | |
| (E) 11-Tetradecenal[2] | | | | 5 | 5 |
| Activ. carbon 300 m²/g | 30 | | | | |
| Activ. carbon 600 m²/g | | 20 | 30 | 20 | 30 |
| Celite SSC | 35 | 40 | 25 | 40 | 25 |
| Irganox 1010 | 5 | 5 | 5 | 5 | 5 |
| U.V. 531 | 5 | 5 | 5 | 5 | 5 |
| Clortex 70[3] | | 10 | 15 | 10 | 25 |
| Polymer PS 50 (RP 10) | 10 | 10 | 10 | 10 | 10 |
| Reax 45A | 5 | 5 | 5 | 5 | 5 |

Notes to Table IX:
[1] Pheromone of *Heliotis armigera*
[2] Pheromone of *Choristoneura fumiferana*
[3] Registered trademark of M/s Caffaro - mixtures of chlorinated derivatives of natural rubber.

As will be apparent, the antioxidants and ultra-violet stabilizers of the present formulations exhibit a high degree of selectivity for achieving the purposes of the formulations.

EXAMPLE 10

Disorientation test (confusion method) carried out on Carpocapsa pomonella (*Laspeyresa pomonella*) in Italy.

The test was performed in an apple-orchard (cv. Granny Smith) near Modena-Italy in the summer of 1980. Formulation No. 26 of Example 8 was applied as aqueous suspension from the ground by means of a common sprayer in the dose of 150 l/ha of suspension corresponding to 22.5 g/ha of active substance (pheromone).

The treatment was performed on 24th July and the results were evaluated during August. The efficacy of the confusion method was determined by comparing the number of adult males caught in traps baited with the same pheromone placed inside the treated area with the number of adult males caught in analogous traps placed about 110 m outside the treated area (check). The data are recorded on the following Table X.

TABLE X

Average number of males of *Carpocapsa pomonella* caught weekly per trap.

| | Weeks of August | | | | Total males caught |
|---|---|---|---|---|---|
| | I | II | II | IV | |
| Traps in treated zone | 0 | 0 | 0 | 0 | 0 |
| Check traps | 11 | 11 | 10 | 2 | 34 |

EXAMPLE 11

Disorientation test (confusion method) carried out on Carpocapsa pomonella (*Laspeyresia pomonella*) in Romania.

The test was performed in an apple-orchard (cv. Johnatan Red) near Prahova (Romania) in the summer of 1980. Formulation No. 26 of Example 8 was applied as aqueous suspension from the ground by means of a common sprayer in the dose of 200 l/ha of suspension corresponding to 20 g/ha of active substance (pheromone).

An area of about 1 ha was treated on 6th June and on 31st July 1980. In the treated area 6 traps were placed.

In an adjacent untreated area 6 other traps were placed (Test 1) as a check. Further traps (Test 2 and Test 3) were placed in an apple-orchard about 100 meters distant from the treated area.

The efficacy of the confusion method was determined by comparing the number of adult males caught in the traps placed inside the treated area and baited with the same pheromone, with the number of adult males caught in the check traps.

The number of captures was controlled till the 2nd November 1980, and the results are reported in the following Table XI.

TABLE XI

Number of males of *Laspeyresia pomonella* caught in the traps from 6th June to 2nd November 1980 (treatments on 6th June and 31st July 1980).

| Traps position | Number of traps | Total number of males caught | Average number of males caught per trap |
|---|---|---|---|
| Treated area | 6 | 37 | 6.16 |
| Adjacent area (Test 1) | 6 | 159 | 26.5 |
| Distant area (Test 2) | 2 | 159 | 79.5 |
| Distant area (Test 3) | 1 | 139 | 139 |

EXAMPLE 12

Disorientation test (confusion method) carried out on *Heliothis virescens* in Brazil.

The test was performed in an area of 9450 m² sowed with cotton in the Estado de São Paolo-Brazil in the period 23rd January–14th February, 1981.

The following formulation (N° 33) in wettable powder was prepared.

| Formulation N° 33 | |
|---|---|
| (Z)-11-hexadecen-1-al[a] | 2.5% by weight |
| (Z)-9-tetradecen-1-al[b] | |
| "Irganox 1010" | 5% by weight |
| "UV 531" | 5% by weight |
| "Polymer PS 50" | 10% by weight |
| "Reax 45 A" | 5% by weight |
| Activated carbon (650 m²/g) | 20% by weight |
| "Chlortex 70" | 30% by weight |
| "Celite SSC" | 22.5% by weight |

[a, b]Components of the sex pheromone of *Heliothis virescens* used in ratio a:b = 10:1.

Formulation N° 33 was distributed in the form of aqueous dispersion (150 l/ha) by means of common sprayers so as to reach a dose of 15 g/ha of pheromone.

After a preliminary treatment with the scope of determining the efficacy of the traps and the presence of infestation, two treatments were performed on Jan. 23 and Feb. 2, 1981 respectively.

The efficacy of the confusion method was determined by comparing the number of males of *Heliothis virescens* caught in three traps baited with the same pheromone and placed in the treated area (traps $A_1$, $A_2$ and $A_3$) and the number of males caught in three analogous traps placed in an adjacent untreated area of 9,450 m² sowed with cotton (traps $B_1$, $B_2$ and $B_3$, checks).

The results are recorded on the following Table XII.

TABLE XII

Number of males of *Heliothis virescens* caught in the observed period

| Traps[1] | Insects caught from 1/23/81[2] to 2/2/81 | Total | Insects caught from 2/2/81[2] to 2/14/81 | Total |
|---|---|---|---|---|
| $A_1$ | 1 | 1 | 2 | 3 |
| $A_2$ | 0 | | 0 | |
| $A_3$ | 0 | | 1 | |
| $B_1$ | 0 | 5 | 2 | 11 |
| $B_2$ | 3 | | 7 | |
| $B_3$ | 2 | | 2 | |

Notes to Table XII
[1]Traps $A_1$–$A_3$ were placed inside the treated area, traps $B_1$–$B_3$ were placed in an untreated adjacent area.
[2]Date of the treatment.

What we claim is:

1. A solid formulation comprising a sex pheromone of insects as an active substance, a carrier composed of a mixture of an inert material having absorbing properties and of an inert material having adsorbing properties as main vehicle, a wetting agent, a dispersant, a sticker, an ultraviolet stabilizer and an antioxidant, said formulation having the following composition to 100%:

| | | |
|---|---|---|
| A | Active substance - sex pheromone | 0.5–10% by weight |
| B | Inert carrier having absorbing properties consisting essentially of a material selected amongst fossil meal, kaolin and attapulgite | 20–50% by weight |
| C | Inert carrier having adsorbing properties consisting essentially of activated carbon with a specific surface from 300 to 900 m²/g | 10–50% by weight |
| D | Mixture of polyoxyethylated alkylphenol (1–10% by weight), sodium polymethacrylate (50–94% by weight) and sodium lignosulphonate (5–40% by weight), the total being 100% | 5–15% by weight |
| E | U.V. Stabilizer consisting of derivatives of benzophenone having stabilizing properties | 0.5–10% by weight |
| F | Antioxidant selected amongst the esters of 3-(3,5-di-tert.butyl-4-hydroxy-phenyl)-propionic acid with stearic alcohol or with pentaerithritol (tetrakis ester) | 0.5–10% by weight |

2. A formulation according to claim 1, in which the active substance is present in an amount of about 5% by weight.

3. A formulation acccording to claim 1, also comprising from 10% to 30% by weight of a film-forming resin, selected amongst terpene polymers and chlorinated natural rubber the total being 100%.

4. A formulation according to claim 1, in which the active substance is (Z)-11-hexadecenal, pheromone of *Heliothis armigera*.

5. A formulation according to claim 1, in which the active substance is (E,E)-8,10-dodecadienol, pheromone of *Laspeyresia pomonella*.

6. A formulation according to claim 1, in which the active substance is (E)-11-tetradecenal, pheromone of *Choristoneura fumiferana*.

7. A formulation according to claim 1, in which the active substance is (Z,E)-9,11-tetradecadienyl acetate, pheromone of *Spodoptera littoralis*.

8. A formulation according to claim 1, in which the active substance is (Z)-11-tetradecenyl acetate, pheromone of *Archips podanus*.

9. A formulation according to claim 3, in which the active substance is a mixture of (Z)-11-hexadecen-1-al and (Z)-9-tetradecen-1-al in the ratio 10:1, pheromone of *Heliothis virescens*.

10. A formulation according to claim 1, in which the ultraviolet stabilizer is 2-hydroxy-4-octyloxy-benzophenone.

11. A formulation according to claim 1, in which in the mixture of polyoxyethylated alkylphenol, sodium polymethacrylate and sodium lignosulphonate, the components are present in the relative ratio 1:9:5 by weight.

12. A formulation according to claim 1, in which the polyoxyethylated alkylphenol is polyoxyethylated nonylphenol with a content of ethylene oxide corresponding to 40–80 moles per mole of nonylphenol.

13. A formulation according to claim 1, in which the sodium polymethacrylate has a molecular weight comprised between 10,000 and 40,000.

14. A formulation according to claim 1, in which the sodium lignosulphonate has a degree of sulphonation comprised between 0.5 and 5.

15. A formulation according to claim 1, consisting of

| | | |
|---|---|---|
| A | Sex pheromone | 5% by weight |
| B | fossil meal | 45% by weight |
| C | activated carbon | 25% by weight |
| D | Mixture of nonylphenol polyoxyethylated, sodium polymethacrylate and sodium lignosulphonate in the weight ratio 1:9:5 | 15% by weight |
| E | 2-hydroxy-4-octyloxy-benzophenone | 5% by weight |
| F | Ester of 3-(3,5-di-tert.butyl-4-hydroxyphenyl)-propionic acid with stearic alcohol or with pentaerithritol (tetrakis ester) | 5% by weight |

16. A formulation according to claim 1, consisting of

| | | |
|---|---|---|
| A | Sex pheromone | 5% by weight |
| B | fossil meal | 30% by weight |
| C | activated carbon | 40% by weight |
| D | Mixture of nonylphenol polyoxyethylated, sodium polymethacrylate and sodium lignosulphonate in the weight ratio 1:9:5 | 15% by weight |
| E | 2-hydroxy-4-octyloxy-benzophenone | 5% by weight |
| F | Ester of 3-(3,5-di-tert.butyl-4-hydroxyphenyl)-propionic acid with stearic alcohol or with pentaerithritol (tetrakis ester) | 5% by weight |

17. A formulation according to claim 1, consisting of

| | | |
|---|---|---|
| A | Sex pheromone | 5% by weight |
| B | fossil meal | 35% by weight |
| C | activated carbon | 35% by weight |
| D | Mixture of nonylphenol polyoxyethylated, sodium polymethacrylate and sodium lignosulphonate in the weight ratio 1:9:5 | 15% by weight |
| E | 2-hydroxy-4-octyloxy-benzophenone | 5% by weight |
| F | Ester of 3-(3,5-di-tert.butyl-4-hydroxyphenyl)-propionic acid with stearic alcohol or with pentaerithritol (tetrakis ester) | 5% by weight |

18. A formulation according to claim 1, consisting of

| | | |
|---|---|---|
| A | Sex pheromone | 5% by weight |
| B | Kaolin | 45% by weight |
| C | Activated carbon | 25% by weight |
| D | Mixture of nonylphenol polyoxyethylated, sodium polymethacrylate and sodium lignosulphonate in the weight ratio 1:9:5 | 15% by weight |
| E | 2-hydroxy-4-octyloxy-benzophenone | 5% by weight |
| F | Ester of 3-(3,5-di-tert.butyl-4-hydroxyphenyl)-propionic acid with stearic alcohol or with pentaerithritol (tetrakis ester) | 5% by weight |

19. A formulation according to claim 1, consisting of

| | | |
|---|---|---|
| A | Sex pheromone | 5% by weight |
| B | Attapulgite | 45% by weight |
| C | Activated carbon | 25% by weight |
| D | Mixture of nonylphenol polyoxyethylated, sodium polymethacrylate and sodium lignosulphonate in the weight ratio 1:9:5 | 15% by weight |
| E | 2-hydroxy-4-octyloxy-benzophenone | 5% by weight |
| F | Ester of 3-(3,5-di-tert.butyl-4-hydroxyphenyl)-propionic acid with stearic alcohol or with pentaerithritol (tetrakis ester) | 5% by weight |

20. A formulation according to claim 3, consisting of

| | | |
|---|---|---|
| A | Sex pheromone | 2.5% by weight |
| B | Fossil meal | 22.5% by weight |
| C | Activated carbon | 20% by weight |
| D | Mixture of nonylphenol polyoxyethylated, sodium polymethacrylate and sodium lignosulphonate in the weight ratio 1:9:5 | 15% by weight |
| E | 2-hydroxy-4-octyloxy-benzophenone | 5% by weight |
| F | Ester of 3-(3,5-di-tert.butyl-4-hydroxyphenyl)-propionic acid with stearic alcohol or with pentaerithritol (tetrakis ester) | 5% by weight |
| G | Chlorinated natural rubber | 30% by weight. |

21. A method of controlling harmfull species of insects by distributing in the infested area the insect sex pheromone so as to prevent copulation, characterized in that an effective amount of a formulation according to claim 1 is distributed in the infested area.

* * * * *